US011337647B2

(12) United States Patent
Reddy et al.

(10) Patent No.: US 11,337,647 B2
(45) Date of Patent: May 24, 2022

(54) QUANTIFICATION OF IN VIVO METABOLITE

(71) Applicant: The Trustees of The University of Pennsylvania, Philadelphia, PA (US)

(72) Inventors: Ravinder Reddy, Gladwynne, PA (US); Ravi Prakash Reddy Nanga, Philadelphia, PA (US); Hari Hariharan, Mount Laurel, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1020 days.

(21) Appl. No.: 14/782,472

(22) PCT Filed: Apr. 4, 2014

(86) PCT No.: PCT/US2014/032990
§ 371 (c)(1),
(2) Date: Oct. 5, 2015

(87) PCT Pub. No.: WO2014/165766
PCT Pub. Date: Oct. 9, 2014

(65) Prior Publication Data
US 2016/0051188 A1 Feb. 25, 2016

Related U.S. Application Data

(60) Provisional application No. 61/809,193, filed on Apr. 5, 2013.

(51) Int. Cl.
*A61B 5/00* (2006.01)
*A61B 5/055* (2006.01)
(Continued)

(52) U.S. Cl.
CPC ............ *A61B 5/4848* (2013.01); *A61B 5/055* (2013.01); *A61B 5/14546* (2013.01);
(Continued)

(58) Field of Classification Search
CPC ....................... G01R 33/5605; G01R 33/4828; G01R 33/56; G01R 33/5601–567; G01R 33/46; A61B 5/055; A61B 6/481; C12Q 1/6886
See application file for complete search history.

(56) References Cited

U.S. PATENT DOCUMENTS

| | | | | |
|---|---|---|---|---|
| 4,678,995 | A * | 7/1987 | Avison | ............... G01R 33/4828 324/309 |
| 2002/0101238 | A1* | 8/2002 | Watanabe | .......... G01R 33/4608 324/309 |

(Continued)

OTHER PUBLICATIONS

Rothman et al., "Localized 1H NMR measurements of γ-aminobutyric acid in human brain in vivo", Proc. Natl. Acad. Sci. USA, vol. 90, pp. 5662-5666, Jun. 1993 Neurobiology (Year: 1993).*

(Continued)

*Primary Examiner* — Joseph M Santos Rodriguez
(74) *Attorney, Agent, or Firm* — BakerHostetler LLP

(57) ABSTRACT

A magnetic resonance pulse sequence technique may acquire a water reference spectrum and two water suppressed metabolite spectra and with frequency selective inversion pulse centered at either single frequency, at multiple frequencies, or in a single acquisition. Subtraction of the inverted from non-inverted water suppressed metabolite spectrum results in single or a combination of specific metabolite peak/peaks alone with a flat baseline for easier quantification.

19 Claims, 6 Drawing Sheets

(51) Int. Cl.

| | | |
|---|---|---|
| *G01R 33/56* | (2006.01) | |
| *A61M 5/00* | (2006.01) | |
| *A61B 5/145* | (2006.01) | |
| *G01R 33/46* | (2006.01) | |
| *G01R 33/483* | (2006.01) | |

(52) U.S. Cl.
CPC .......... *A61B 5/4064* (2013.01); *A61B 5/4839* (2013.01); *A61B 5/4866* (2013.01); *A61M 5/007* (2013.01); *G01R 33/46* (2013.01); *G01R 33/483* (2013.01); *G01R 33/5601* (2013.01); *G01R 33/5605* (2013.01); *A61B 2560/0475* (2013.01); *A61B 2576/00* (2013.01)

(56) References Cited

U.S. PATENT DOCUMENTS

| | | |
|---|---|---|
| 2007/0134159 A1 | 6/2007 | Dixon et al. |
| 2009/0176218 A1 | 7/2009 | Cheng et al. |
| 2010/0290997 A1 | 11/2010 | Li et al. |
| 2012/0019245 A1 | 1/2012 | Reddy et al. |
| 2012/0108944 A1* | 5/2012 | Turek .................... A61B 5/055 600/410 |
| 2013/0195768 A1 | 8/2013 | Aime et al. |
| 2014/0087362 A1 | 3/2014 | Szalay et al. |

OTHER PUBLICATIONS

Balchandani, et al., "Fat Suppression for H MRSI at 7T Using Spectrally-Selective Adiabatic Inversion Recovery," Magn Reson Med., May 2008, 59(5), 980-988.

Cai, et al. "Breast Cancer Redox Heterogeneity Detectable with Chemical Exchange Saturation Transfer (CEST) MRI," Mol. Imaging Bioi., May 9, 2014, 10 pgs.

Cantor, et al. "Cancer Cell Metabolism: One Hallmark, Many faces," Cancer Discov, Sep. 25, 2012, vol. 2(10), 881-898.

Li, et al. "Imaging Mitochondrial Redox Potential and its Possible Link to Tumor Metastatic Potential," J Bioenerg Biomembr, Dec. 1, 2012, vol. 44, pp. 645-653.

Penner, et al. "Metabolite Nulling to measure the Macromolecule Baseline for Quantitative $^1$H Magnetic Resonance Spectroscopy at 7 Tesla," Proc. Inti. Soc. Mag. Reson. Med., 2010, p. 911.

Periasamy, et al "Tea polyphenols Modulate Antioxidant Redox System on Cisplatin-Induced Reactive Oxygen Species Generation in a Human Breast Cancer Cell." Basic Clin Pharmacal Toxicol, Jan. 24, 2013, vol. 112, 374-384.

Ratnakar, et al. "Europium(III) DOTA-tetraamide Complexes as Redox-Active MRI Sensors," J. Am Chem. Soc, Mar. 23, 2012, vol. 134, 5798-5800.

Schafer et al. "Redox Environment of the Cell as Viewed Through the Redox State of the Glutathione Disulfide/Glutathione Couple," Free Radic Bioi Med, Jun. 1, 2001, vol. 30, 1191-1212.

* cited by examiner

QUANTIFICATION OF IN VIVO METABOLITE

CROSS-REFERENCE TO RELATED APPLICATIONS

This application is the National Stage of International Application No. PCT/US2014/032990, filed Apr. 4, 2014, which claims the benefit of U.S. Provisional Application No. 61/809,193 filed Apr. 5, 2013, the disclosures of which are incorporated herein by reference in their entireties for any and all purposes.

GOVERNMENT RIGHTS

This invention was made with government support under grant numbers EB015893, DA032256, and KG081069 awarded by the National Institutes of Health. The government has certain rights in the invention.

TECHNICAL FIELD

The technical field generally relates to magnetic resonance and relates to chemical exchange saturation transfer imaging techniques.

BACKGROUND

Chemical Exchange Saturation Transfer (CEST) is a technique that provides an indirect way of detecting the signal from exchangeable protons with bulk water in magnetic resonance imaging (MRI). CEST imaging uses an off-resonance saturation pulse at the resonance frequency of exchanging protons to null the signal from exchangeable protons in order to indirectly decrease bulk water signal through chemical exchange, creating a detectable contrast from bulk waters.

Quantification of the metabolites from proton magnetic resonance spectroscopy ($^1$HMRS) of human brain is often confounded by overlap with varying compositions of lipids and macromolecules. Level of this contamination varies across the brain and introduces operator bias and thus reduces the reproducibility of the measurements, which poses a significant problem in acute drug studies. With prior methods it is difficult to measure these metabolites with MRS due to overlapping signals from lipids and other molecules.

SUMMARY

Subtraction of the inverted from non-inverted water suppressed metabolite spectrum results in single or a combination of specific metabolite peak/peaks alone with a flat baseline for easier quantification. In an embodiment, device comprises a processor adapted to execute computer-readable instructions and a memory communicatively coupled to said processor. The said memory having stored computer-readable instructions that when executed by the processor, cause the processor to perform operations including receiving a first measurement for a metabolite group inverted spectra using magnetic resonance in a volume, receiving a second measurement for the metabolite group without inversion using magnetic resonance in the volume, and quantifying the metabolite group in the area based on the difference of the first measurement and the second measurement.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying drawings wherein.

DETAILED DESCRIPTION OF ILLUSTRATIVE EMBODIMENTS

Quantification of metabolites from proton magnetic resonance spectroscopy ($^1$HMRS) of human brain is often confounded by overlap with varying compositions of lipids and macromolecules. The level of this contamination varies across the brain and introduces operator bias. Thus, the reproducibility of the measurements is reduced, which poses a significant problem in acute drug studies. With prior methods it is difficult to measure these metabolites with MRS due to overlapping signals from lipids and other molecules. Disclosed herein is a strategy for the quantification of the in vivo glutamate/glutamine (Glx), which is applicable to other metabolites.

The magnetic resonance pulse sequence inversion technique disclosed herein can acquire a water reference spectrum and two water suppressed metabolite spectra and with frequency selective inversion pulse centered at single frequency (e.g. 2.35 ppm for glutamate), at multiple frequencies, or the same inversion pulse centered at a frequency offset that is symmetrically opposite from water to that of the metabolite (e.g. 7.05 ppm for glutamate) in a single acquisition. Subtraction of the inverted from non-inverted water suppressed metabolite spectrum results in single or a combination of specific metabolite peak/peaks alone with a flat baseline for easier quantification.

The disclosed inversion technique may be used in the field of clinical MRS/MRI, small animal MRS/MRI, and clinical trials of acute drug studies in animals and in humans (e.g., monitoring or determining drug effectiveness), among other things. For example, with regard to glutamate/glutamine, the metabolism cycle is significant for neurological function, and glutamate metabolism and oxidative stress are closely correlated. Imbalanced metabolism and excess reactive oxygen species generation may result in a range of disorders, such as Alzheimer's disease, Parkinson's disease, aging, and many neural disorders. The disclosed method increases the consistency of the measurements and may allow for less bias in diagnosis of disorders and effectiveness of drugs.

Figure 1:
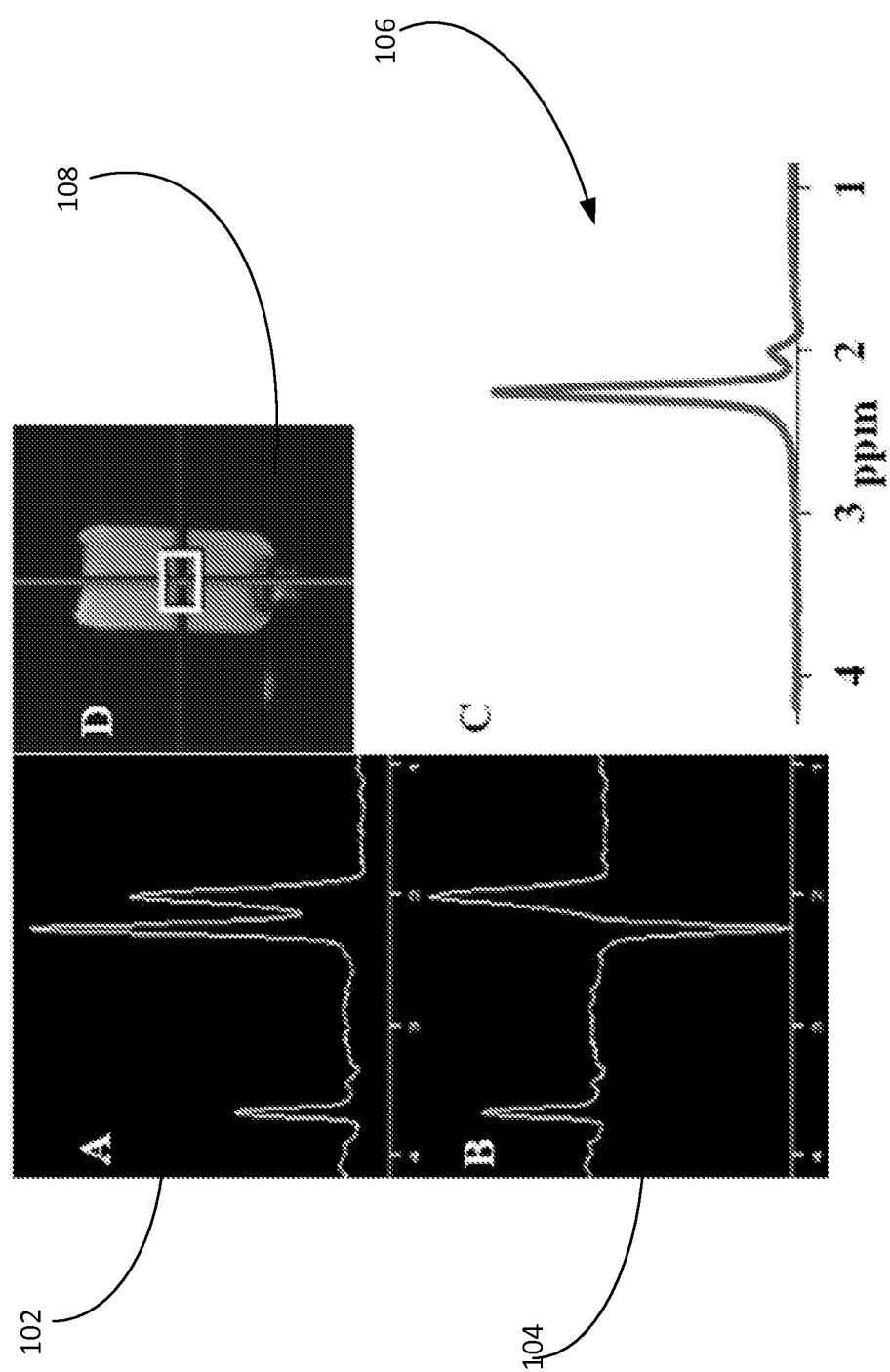
FIG. 1 displays magnetic resonance related measurements of a phantom.
Figure 2:
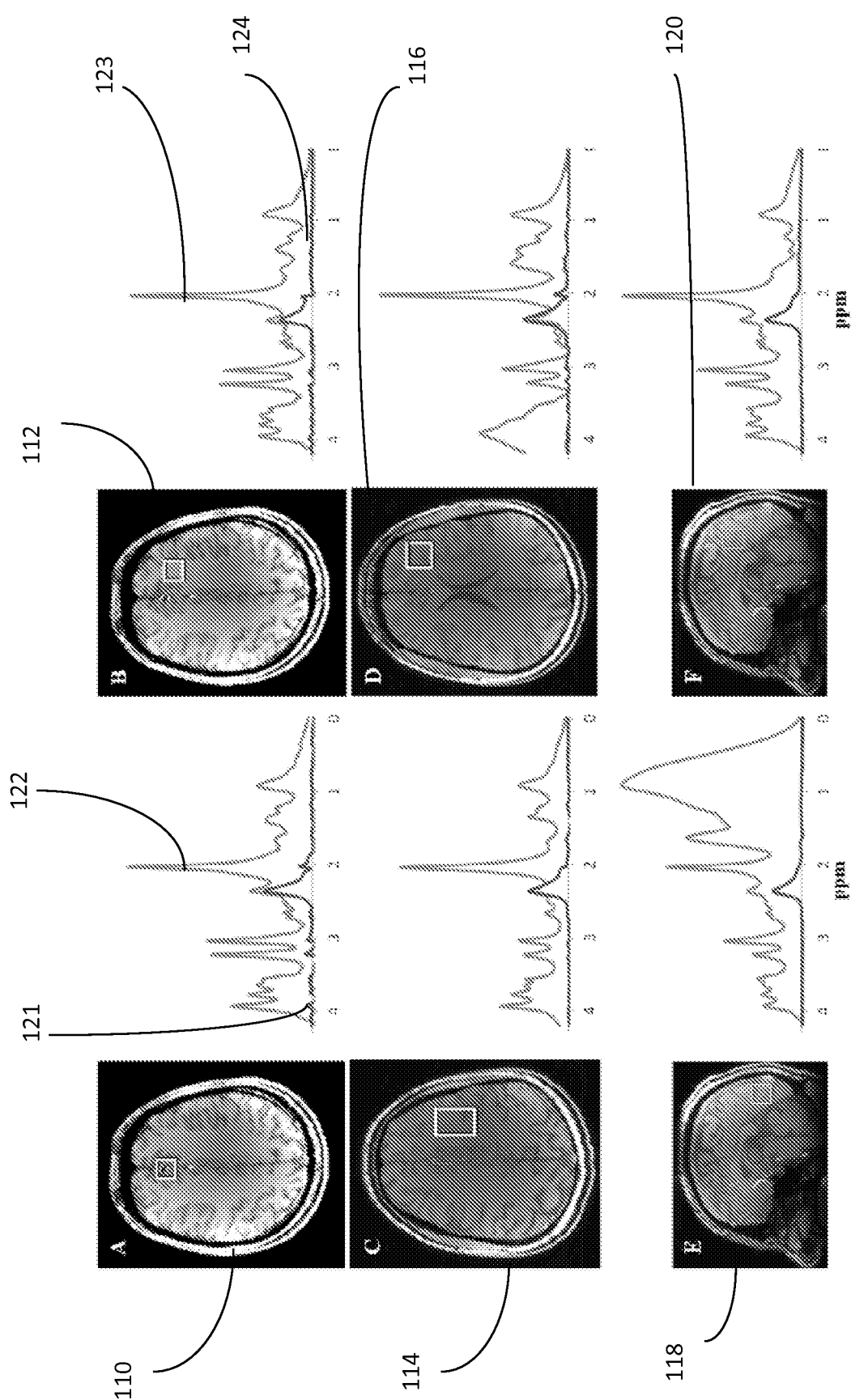
FIG. 2 displays magnetic resonance related measurements of six different volex locations.

FIG. 1 displays water-suppressed non-inverted graph 102 and inverted metabolite spectra graph 104 obtained using MRS for an experiment keying on glutamate. Graph 106 shows a difference spectrum of graph 102 and graph 104 obtained on Glutamate phantom 108. In the experiment, $^1$HMRS (proton magnetic resonance spectroscopy) was performed on Glutamate phantom at room temperature and on normal healthy volunteers (aged 19-33 years) using a 7T whole body scanner with a vendor supplied 32-Channel head coil. FIG. 2 shows images with outlines of volumes of interest and $^1$HMRS data for six different voxel locations. Next to the images of the brain in FIG. 2 are graphs that show measurements using the traditional method (e.g., top line 122) and the quantification method involving inversion disclosed herein (e.g., bottom line 121). The y-axis of the graphs may be of arbitrary units while the x-axis is in parts per million (ppm). In the experiment, several regions of the brain were chosen to illustrate that the quantification method works well in multiple regions.

FIG. 2 displays mid-frontal grey matter (MFGM) 110 with a volume of 15×15×15 mm$^3$, left frontal white matter LFWM 112 with a volume of 15×15×15 mm$^3$, left dorso-lateral prefrontal cortex (LDLPFC) with a volume of 20×30×20 mm$^3$, left prefrontal cortex (LPFC) 116 with a volume of 20×20×20 mm$^3$, occipital cortex (OCC) 118 with a volume of 20×30×20 mm$^3$, and posterior cingulate cortex (PCC) 120 with a volume of 20×30×20 mm$^3$. The top lines in the graphs are the traditional spectra showing spectral overlap with multiple metabolites (difficult quantification—e.g., line 122 or line 123) and bottom lines in the graphs are the inversion method spectra (showing simplification bottom line—e.g., line 121 and line 124). Automated shimming of the $B_0$ field was performed on the voxel in order to obtain localized water line width of ~30 Hz or less. Single voxel spectra (SVS) for Glx were obtained with a custom sequence that acquires a water reference spectrum, a water suppressed metabolite spectrum, and a water suppressed metabolite spectrum with a narrow band frequency inversion in a single acquisition using the following parameters: number of points=2048, averages=8/32/32, repetition time (TR)=3000 ms, and echo time (TE)=21 ms. Total acquisition time to obtain the spectra were 4 minutes.

Frequency selective editing pulses were used to invert Glutamate —CH$_2$ protons attached to β-carbon (at 2.35 ppm). The inversion width used was 20 Hz, which was based on the line-width of water after eddy current compensation (usually varies from ~18-21 Hz). Each subject was scanned twice for two different voxels, to examine between day reproducibility in Glx concentrations across time and the voxel was positioned by using automated custom-built software for the second scan, to maintain the consistency in voxel placement. For post-processing the raw multi-channel time domain data from the scanner was used. From the water reference data, channel wise time dependent phase shifts due to eddy current and amplitude scale factors were obtained and saved.

All three spectra were obtained after channel wise eddy current correction and adaptive combination. Subtraction of inverted from non-inverted water suppressed spectra results in twice the amplitude of Glx signal. Amplitude of the Glx peak at 2.35 ppm, thus obtained from the areas of interest in brain were halved before being fitted as two peaks (since there may be a slight contamination from γ-CH$_2$ protons of Glutamate at 2.13 ppm) by Lorentzian functions with non-linear least squares fitting followed by integration and then normalized by water reference signal for absolute quantification of Glx. Metabolite peaks from water suppressed non-inverted spectrum were fitted as Lorentzian functions with non-linear least squares fitting by taking into account the prior knowledge of the ten macromolecular peaks and 15 metabolite peaks over the frequency range of 0.5 to 4.3 ppm followed by integration and then normalized by water reference signal for absolute quantification of Glx. Base SNR for both the spectra in all cases were greater than 500.

Figure 3:
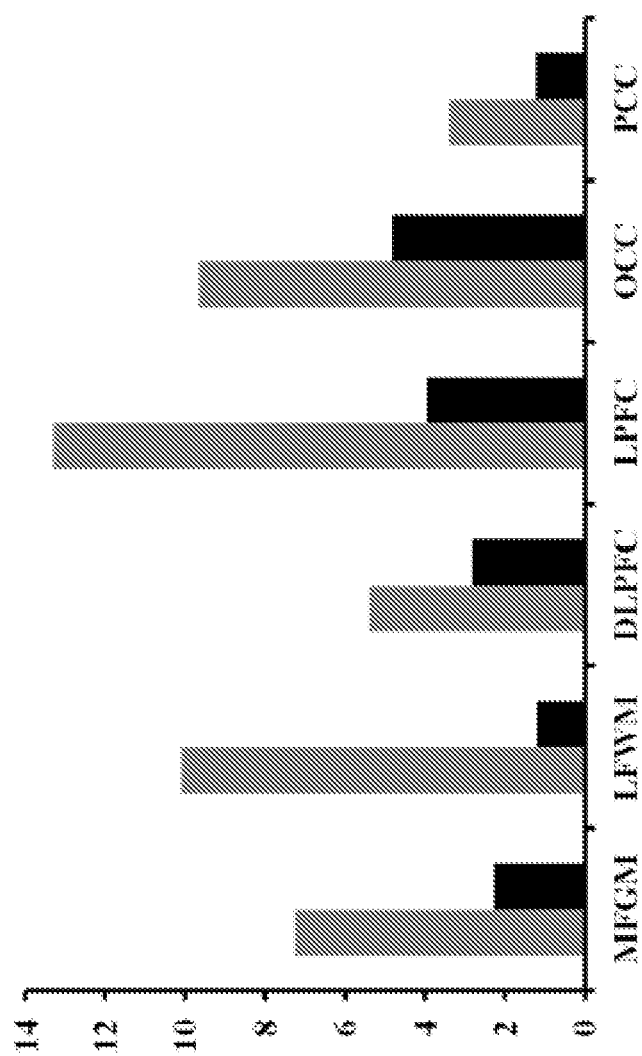
FIG. 3 displays relative changes in absolute glutamate/glutamine.

The concentrations of Glu at 2.26 ppm for the 9.3 mM Glutamate phantom from water suppressed non-inverted spectrum and from selective frequency inversion method were 9.27 mM and 9.79 mM, respectively (see FIG. 1). The concentrations of Glx at 2.35 ppm from water suppressed non-inverted spectrum and from selective frequency inversion method for both the scans from the normal healthy volunteers are tabulated in Table 1. FIG. 3 illustrates the relative changes in absolute Glx concentrations from between day scans for water suppressed non-inverted spectra (grey) and from selective frequency inversion method (black). The relative changes in absolute Glx concentration from between day scans as shown in FIG. 3 for voxel positioned in different anatomical areas are lower for selective frequency inversion method when compared to traditional water suppressed metabolite spectra with contaminations.

TABLE 1

| | Glx Concentrations | | | | | |
|---|---|---|---|---|---|---|
| | Traditional method | | | Inversion method | | |
| | Glx (mM) | | Rel | Glx (mM) | | Rel |
| Voxel | Scan 1 | Scan 2 | Ch (%) | Scan 1 | Scan 2 | Ch (%) |
| MFGM | 12.97 | 13.91 | 7.25 | 14.51 | 14.18 | 2.27 |
| LFWM | 10.18 | 11.21 | 10.12 | 13.25 | 13.09 | 1.21 |
| LDLPFC | 12.05 | 12.7 | 5.39 | 14.21 | 14.61 | 2.81 |
| LPFC | 9.48 | 8.22 | 13.29 | 15.93 | 15.3 | 3.95 |
| OCC | 13.66 | 14.98 | 9.66 | 16.13 | 15.35 | 4.84 |
| PCC | 13.83 | 13.36 | 3.40 | 14.7 | 14.52 | 1.22 |

Disclosed herein is the implementation of a selective frequency inversion method that simplifies the quantification of metabolites, such as Glx, in in vivo brain spectra. The inversion approach shows within subject variability of 1% to 5%, while the conventional water suppressed metabolite spectra approach shows a larger range of 3% to 13% for voxels positioned in different regions of the brain.

Figure 4:
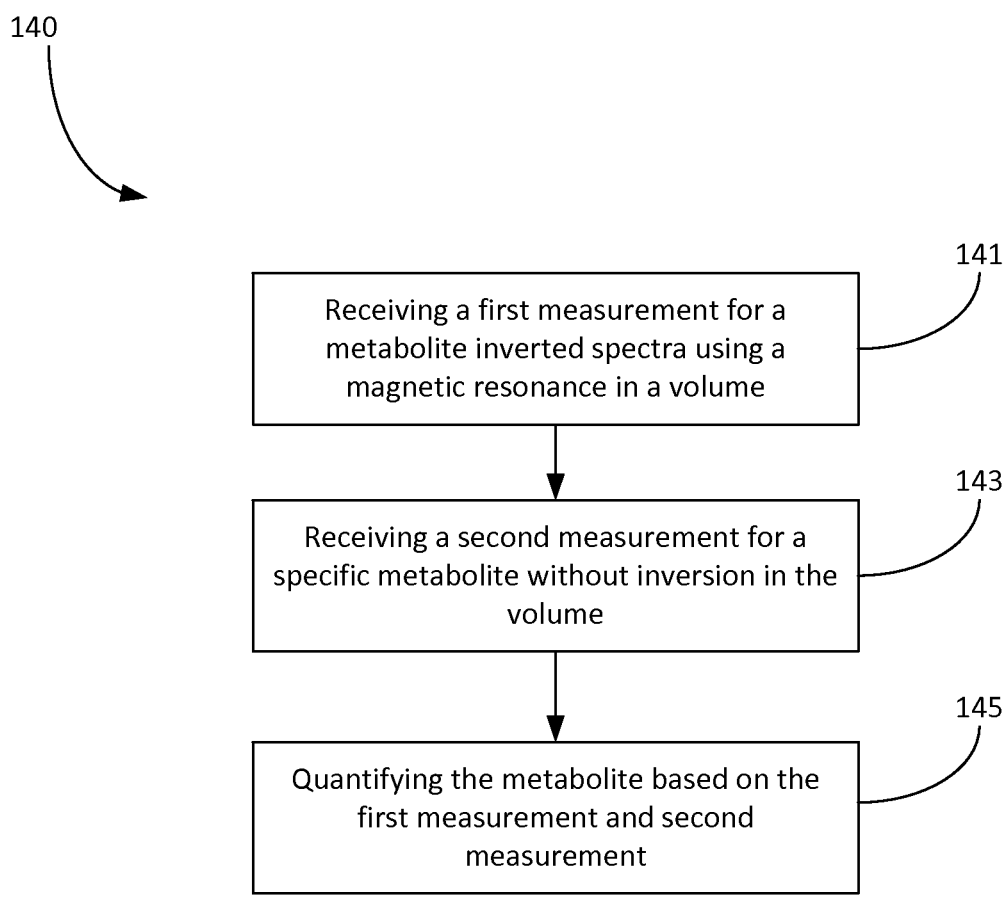
FIG. 4 illustrates an exemplary block diagram for quantification of an in vivo metabolite.

FIG. 4 is a block diagram of an exemplary method 140 illustrating quantification of an in vivo metabolite. At block 141, a first measurement for a metabolite inverted spectra is obtained using magnetic resonance in a volume (e.g., a selected area of the brain, as illustrated in FIG. 2). The metabolite may be any specific metabolite or combination of metabolites. For example, the metabolite may be glutamine, glutamate/glutamine (Glx), creatine (Cr), or any other metabolite of interest. In addition, the method may be applied to a combination of metabolites, e.g., a combination (i.e., grouping) of Cr and Glx. The method may be applied to a combination in order to reduce overall acquisition time and get quantitative results from more than one metabolite in a single procedure. At block 143, a second measurement for the metabolite without inversion is obtained using magnetic resonance in approximately the same volume. At block 145, the metabolite is quantified based on the difference of the first measurement and the second measurement.

Figure 5:
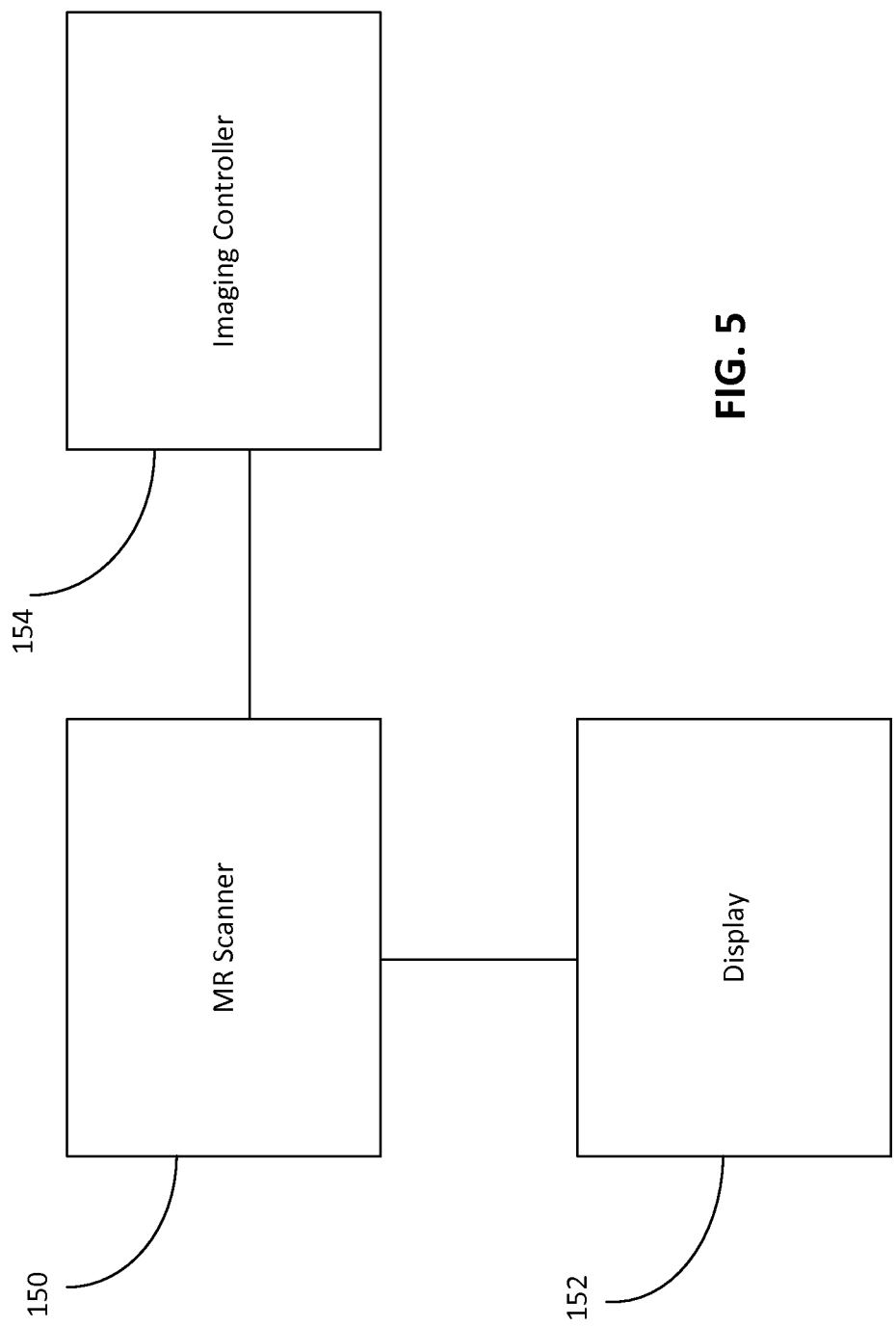
FIG. 5 illustrates a conventional MR scanner that displays the obtained MR images on a display under control of an imaging controller programmed to implement any or all of the imaging pulse sequences and imaging protocols that may relate to CEST described herein.

FIG. 5 illustrates in rudimentary form a conventional MR scanner 150 that displays the obtained MR images on a display 152. Imaging controller 154 includes a processor programmed to implement any or all of the imaging pulse sequences and imaging protocols described herein. Accordingly, any such modifications are intended to be included within the scope of this invention as defined by the following exemplary claims.

Figure 6:
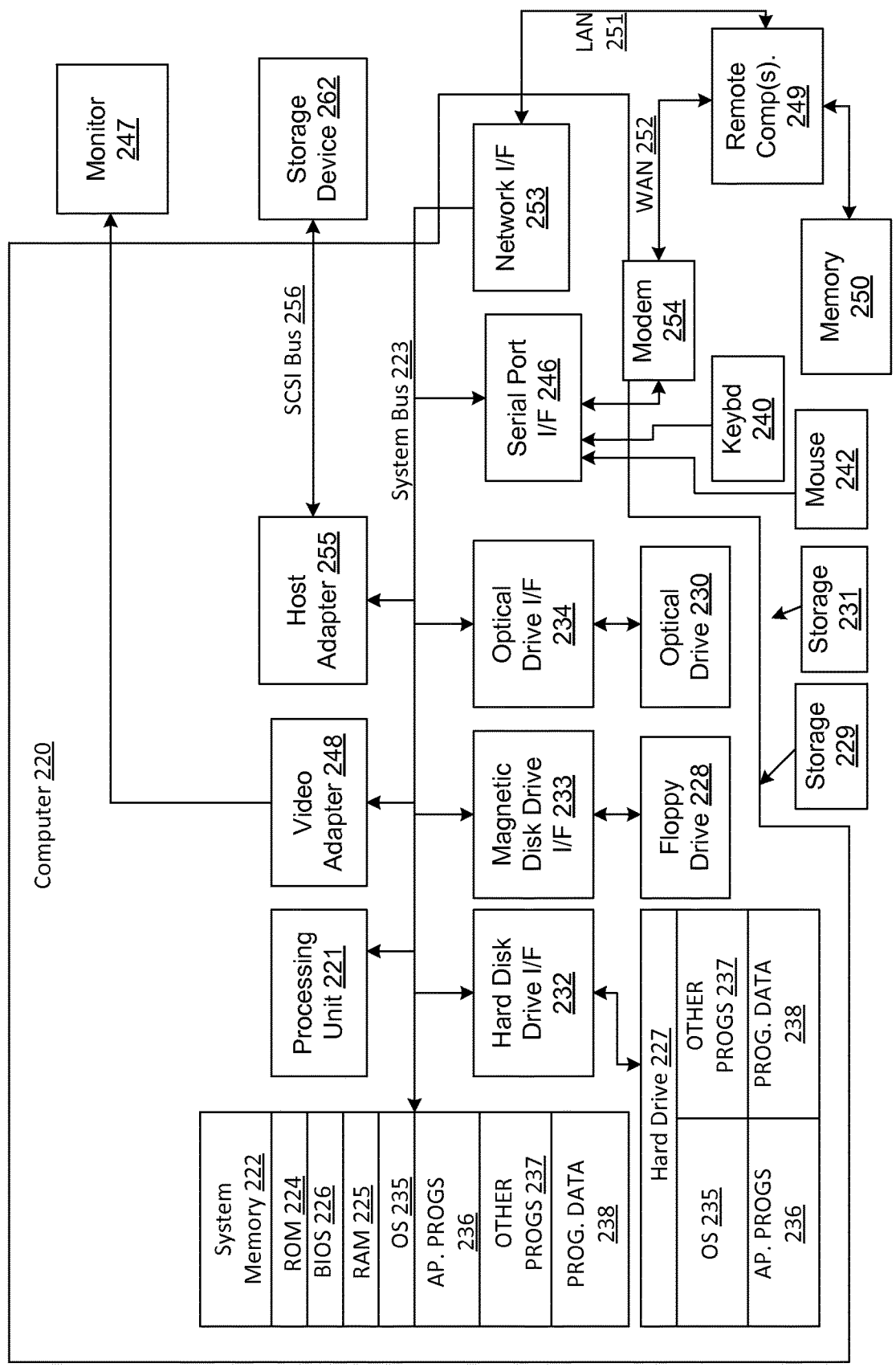
FIG. 6 is an exemplary block diagram representing a general purpose computer system in which aspects of the methods and systems disclosed herein or portions thereof may be incorporated.

FIG. 6 and the following discussion are intended to provide a brief general description of a suitable computing environment in which the methods and systems disclosed herein and/or portions thereof may be implemented. Although not required, the methods and systems disclosed herein may be described in the general context of computer-executable instructions, such as program modules, being executed by a computer, such as a client workstation, server or personal computer. Generally, program modules include routines, programs, objects, components, data structures and the like that perform particular tasks or implement particular abstract data types. Moreover, it should be appreciated the methods and systems disclosed herein and/or portions thereof may be practiced with other computer system configurations, including hand-held devices, multi-processor systems, microprocessor-based or programmable consumer electronics, network PCs, minicomputers, mainframe computers and the like. A processor may be implemented on a single-chip, multiple chips or multiple electrical components with different architectures. The methods and systems disclosed herein may also be practiced in distributed computing environments where tasks are performed by remote processing devices that are linked through a communications network. In a distributed computing environment, program modules may be located in both local and remote memory storage devices.

FIG. 6 is a block diagram representing a general purpose computer system (e.g., an MR scanner or device connected therewith) in which aspects of the methods and systems disclosed herein and/or portions thereof may be incorporated. As shown, the exemplary general purpose computing system includes a computer 2220 or the like, including a processing unit 2221, a system memory 2222, and a system bus 2223 that couples various system components including the system memory to the processing unit 2221. The system bus 2223 may be any of several types of bus structures including a memory bus or memory controller, a peripheral bus, and a local bus using any of a variety of bus architectures. The system memory includes read-only memory (ROM) 2224 and random access memory (RAM) 2225. A basic input/output system 2226 (BIOS), containing the basic routines that help to transfer information between elements within the computer 2220, such as during start-up, is stored in ROM 2224.

The computer 2220 may further include a hard disk drive 2227 for reading from and writing to a hard disk (not shown), a magnetic disk drive 2228 for reading from or writing to a removable magnetic disk 2229, and an optical disk drive 2230 for reading from or writing to a removable optical disk 2231 such as a CD-ROM or other optical media. The hard disk drive 2227, magnetic disk drive 2228, and optical disk drive 2230 are connected to the system bus 2223 by a hard disk drive interface 2232, a magnetic disk drive interface 2233, and an optical drive interface 2234, respectively. The drives and their associated computer-readable media provide non-volatile storage of computer readable instructions, data structures, program modules and other data for the computer 2220. As described herein, computer-readable media is a tangible article of manufacture and thus not a signal per se.

Although the exemplary environment described herein employs a hard disk, a removable magnetic disk 2229, and a removable optical disk 2231, it should be appreciated that other types of computer readable media which can store data that is accessible by a computer may also be used in the exemplary operating environment. Such other types of media include, but are not limited to, a magnetic cassette, a flash memory card, a digital video or versatile disk, a Bernoulli cartridge, a random access memory (RAM), a read-only memory (ROM), and the like.

A number of program modules may be stored on the hard disk, magnetic disk 2229, optical disk 2231, ROM 2224 or RAM 2225, including an operating system 2235, one or more application programs 2236, other program modules 2237 and program data 2238. A user may enter commands and information into the computer 2220 through input devices such as a keyboard 2240 and pointing device 2242. Other input devices (not shown) may include a microphone, joystick, game pad, satellite disk, scanner, or the like. These and other input devices are often connected to the processing unit 2221 through a serial port interface 2246 that is coupled to the system bus, but may be connected by other interfaces, such as a parallel port, game port, universal serial bus (USB), a wireless interface such as Bluetooth, or the like. A monitor 2247 or other type of display device is also connected to the system bus 2223 via an interface, such as a video adapter 2248. In addition to the monitor 2247, a computer may include other peripheral output devices (not shown), such as speakers and printers. The exemplary system of FIG. 6 also includes a host adapter 2255, a Small Computer System Interface (SCSI) bus 2256, and an external storage device 2262 connected to the SCSI bus 2256.

The computer 2220 may operate in a networked environment using logical connections to one or more remote computers, such as a remote computer 2249. The remote computer 2249 may be a personal computer, a server, a router, a network PC, a peer device or other common network node, and may include many or all of the elements described above relative to the computer 2220, although only a memory storage device 2250 has been illustrated in FIG. 6. The logical connections depicted in FIG. 6 include a local area network (LAN) 2251 and a wide area network (WAN) 2252. Such networking environments are commonplace in offices, enterprise-wide computer networks, intranets, and the Internet.

When used in a LAN networking environment, the computer 2220 is connected to the LAN 2251 through a network interface or adapter 2253. When used in a WAN networking environment, the computer 2220 may include a modem 2254 or other means for establishing communications over the wide area network 2252, such as the Internet. The modem 2254, which may be internal or external, is connected to the system bus 2223 via the serial port interface 2246. In a networked environment, program modules depicted relative to the computer 2220, or portions thereof, may be stored in the remote memory storage device. It will be appreciated that the network connections shown are exemplary and other means of establishing a communications link between the computers may be used. Connections discussed herein may be wireless or wireline.

Computer 2220 may include a variety of computer readable storage media. Computer readable storage media can be any available media that can be accessed by computer 2220 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 2220. Combinations of any of the above should also be included within the scope of computer readable media that may be used to store source code for implementing the methods and systems described herein. Any combination of the features or elements disclosed herein may be used in one or more embodiments.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

Although features and elements are described above in particular combinations, one of ordinary skill in the art will appreciate that each feature or element can be used alone or in any combination with the other features and elements. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A method comprising:
   receiving a first measurement for spectra with selective inversion of a metabolite using magnetic resonance in a volume, wherein selective inversion is selective of one or more spectral peaks indicative of the metabolite, wherein selective inversion comprises a spectral inversion that uses one or more frequency selective editing pulses targeting a frequency range comprising the one or more spectral peaks to invert all of the one or more spectral peaks;
   receiving a second measurement for the metabolite without inversion using magnetic resonance in the volume, wherein the second measurement comprises one or more spectral peaks outside of the frequency range;
   determining a difference measurement by subtracting the first measurement from the second measurement resulting in data indicative of the one or more spectral peaks indicative of the metabolite without the one or more spectral peaks outside of the frequency range; and
   quantifying the metabolite in the volume based on the difference measurement.

2. The method of claim 1, wherein the magnetic resonance used is $^1$HMRS.

3. The method of claim 1, wherein the metabolite is glutamate/glutamine (Glx).

4. The method of claim 1, wherein the metabolite is creatine (Cr).

5. The method of claim 1, wherein the first measurement and the second measurement are done in vivo.

6. The method of claim 1, wherein the first measurement and the second measurement are done on a human brain.

7. The method of claim 1, further comprising monitoring a drug in a human based on the quantified metabolite.

8. The method of claim 1, further comprising determining efficacy of a drug based on the quantified metabolite.

9. The method of claim 1, further comprising determining aggressiveness of a tumor based on the quantified metabolite.

10. A device comprising:
    a processor adapted to execute computer-readable instructions; and
    a memory communicatively coupled to said processor, said memory having stored therein computer-readable instructions that when executed by the processor, cause the processor to perform operations comprising:
      receiving a first measurement for a metabolite group inverted spectra using magnetic resonance in a volume, wherein the inverted spectra is selective of one or more spectral peaks indicative of the metabolite group, wherein selective inversion comprises a spectral inversion that uses one or more frequency selective editing pulses targeting a frequency range comprising the one or more spectral peaks to invert all of the one or more spectral peaks;
      receiving a second measurement for the metabolite group without inversion using the magnetic resonance in the volume, wherein the second measurement comprises one or more spectral peaks outside of the frequency range;
      determining a difference measurement by subtracting the first measurement from the second measurement resulting in data indicative of the one or more spectral peaks indicative of the metabolite group without the one or more spectral peaks outside of the frequency range; and
      quantifying the metabolite group in the volume based on the difference measurement.

11. The device of claim 10, wherein the metabolite group comprises glutamate/glutamine (Glx).

12. The device of claim 10, wherein the first measurement and the second measurement are done on a human brain.

13. The device of claim 10, wherein the magnetic resonance used is $^1$HMRS.

14. The device of claim 10, wherein the first measurement and the second measurement are done in vivo.

15. The device of claim 10, wherein the instructions, when executed by the processor, further cause the processor to perform operations comprising determining efficacy of a drug based on the quantified metabolite.

16. The method of claim 1, wherein the frequency range is determined based on spectral data indicative of the metabolite.

17. The device of claim 10, wherein the frequency range is determined based on spectral data indicative of the metabolite group.

18. The device of claim 17, wherein the frequency range is centered at one or more frequencies indicative of the metabolite group.

19. The method of claim 16, wherein the frequency range is centered at one or more frequencies indicative of the metabolite.

\* \* \* \* \*